United States Patent
Masia et al.

[11] Patent Number: 5,844,696
[45] Date of Patent: Dec. 1, 1998

[54] NITRIC ESTERS FROM DERIVATIVES OF 2-(2,6-DIHALOPHENYLAMINO) PHENYLACETOXYACETIC ACID AND THEIR PREPARATION PROCESS

[75] Inventors: Xavier Serra Masia; Joan Pi Sallent, both of Barcelona, Spain

[73] Assignee: Prodes, S.A., Barcelona, Spain

[21] Appl. No.: 634,763

[22] Filed: Apr. 19, 1996

[30] Foreign Application Priority Data

Apr. 19, 1995 [ES] Spain ........................................ 9500756

[51] Int. Cl.$^6$ .................................................. C07C 203/08
[52] U.S. Cl. ............................................................ 558/482
[58] Field of Search .................................... 558/482, 483, 558/487

[56] References Cited

U.S. PATENT DOCUMENTS 5,366,992  11/1994  Sala et al. ................................. 514/409

FOREIGN PATENT DOCUMENTS 0119 932   5/1987   European Pat. Off. .
PCT/EP93/
    01906  3/1994   WIPO .

*Primary Examiner*—Charles T. Jordan
*Assistant Examiner*—John R. Hardee
*Attorney, Agent, or Firm*—Mathews Woodbridge & Collins

[57] ABSTRACT

Nitric esters from derivatives of 2-(2,6-dihalophenylamino) phenylacetoxyacetic acid with the formula (I), where: [A≡F, Cl or Br; X≡O, NH or NR (R≡$C_1$–$C_8$ alkyl); $R_1$ and $R_2$ independently≡$C_1$–$C_8$ alkyl and n is a whole number from 1 to 10. The procedure includes the condensation of 2-(2,6-diahlophenylamino) phenylacetoxyacetic acid with a compound with the formula:

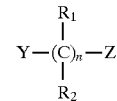

where Y≡OH, $NH_2$ or NHR and Z is Cl, Br or $ONO_2$.

9 Claims, No Drawings

NITRIC ESTERS FROM DERIVATIVES OF 2-(2,6-DIHALOPHENYLAMINO) PHENYLACETOXYACETIC ACID AND THEIR PREPARATION PROCESS

SPECIFICATION

This invention refers to the nitric esters from derivatives of 2-(2,6-dihalophenylamino) phenylacetoxyacetic acid; the invention also refers to the procedures for their preparation.

STATE OF THE ART

An already classical product in the non-esteroid anti-inflammatory group is the sodium salt from the 2-(2,6-dichlorophenylamino) phenylacetic acid. However, it is well known that its use causes severe gastrointestinal and hepatic secondary effects. With the aim of improving this limitation, certain functionalized derivatives with an ester from the nitric acid have been claimed recently (WO 94/04484). These derivatives have been described in the patent mentioned as having an anti-inflammatory activity with less gastric secondary effects.

AIM OF THE INVENTION

The actual petitioner owns patent EP 0 119 932 referred, an AINE, the 2-(2,6-dihalophenylamino) phenylacetoxyacetic acid (Aceclofenaco).

This product, besides having a powerful anti-inflammatory and analgesic activity, presents a very improved gastric tolerance (Drugs and Inflammation, Vol. 32 (1991)) well proved in clinical studies (Clin. Tri. J., 27(1), 12–19 (1990), Cli. Tri. J., 25(2), 144–151 (1988), Curr. Ther. Res., 44(2), 252–256 (1988), Drugs Exp. Clin. Res., 15(1), 47–51 (1989). Due to these qualities, the Aceclofenaco is actually a well known prestigious AINE.

Researches on products related with Aceclofenaco have been carried out with the aim of providing new products that, keeping the advantageous pharmacological qualities of the 2-(2,6-dichlorophenylamino) phenylacetoxyacetic acid, allow the complete elimination of the rest of gastric injuries. The preparation process of the said derivatives of the 2-(2,6-dichlorophenylamino) phenylacetoxyacetic acid are also a target of this invention.

DESCRIPTION OF THE INVENTION

The purpose mentioned in the previous paragraph is obtained by the products of this invention, nitric esters from derivatives of the 2-(2,6-dihalophenylamino) phenylacetoxyacetic acid represented by the general formula I:

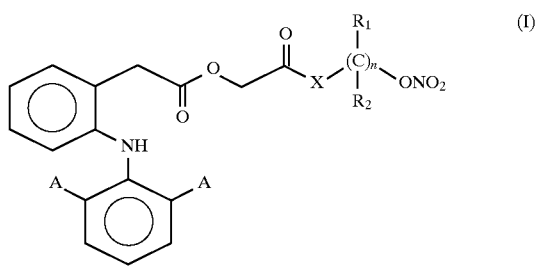

where:
- A is fluorine, chlorine or bromine;
- X means oxygen, NH or NR where R means a linear or branched alkyl chain of 1 to 6 carbon atoms;
- $R_1$ and $R_2$ mean, independently, hydrogen or a linear or branched alkyl chain of 1 to 6 carbon atoms; and n is a number between 1 to 10.

In the compounds of this invention are especially interesting some nitrate compounds of general structure I where A is chlorine, X is oxygen, $R_1$ and $R_2$ are both hydrogen and n is between 2 to 4, and they are represented by the following formula II:

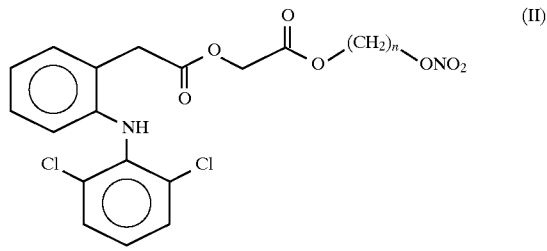

Similarly, it is also especially interesting the nitroester with the general formula I, where A is chlorine, X is NH, $R_1$ and $R_2$ are both hydrogen and n=2, which is represented by formula III:

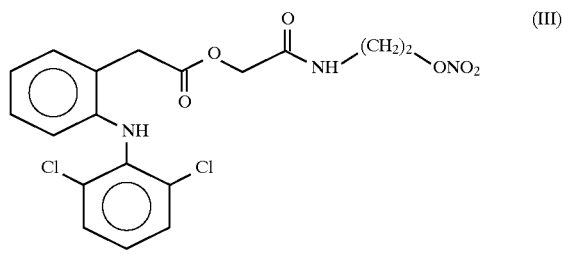

To prepare the nitroesters with the general formula I several procedures can be used, as described below.

a. The first process is to carry out the condensation of the corresponding 2-(2,6-dihalophenylamino) phenylacetoxyacetic acid with the formula IV:

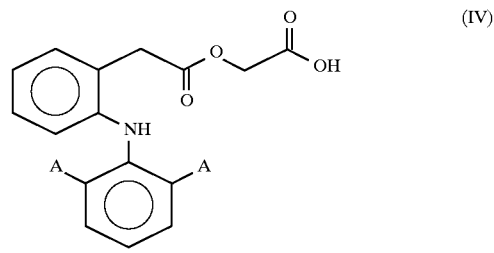

where: A is fluorine, chlorine or bromine, with a derivate with the general formula V:

where Y can be OH, $NH_2$ or NHR being R a linear or branched alkyl chain of 1 to 6 carbon atoms, while $R_1$, $R_2$ and n have the same meaning as described before for the general formula I.

The reaction is carried out by means of a suitable condensation agent like N,N'-dicyclohexylcarbodiimide or N,N'-carbonyl diimidazole in an aprotic solvent generally chlorinated type (chloroform, dichloromethane), ether (tetrahydrofurane) or similar.

b. A second process of preparation consists on the following steps:

i) Condensation of the 2-(2,6-dihalophenylamino) phenylacetoxyacetic acid with the formula IV with a compound with the general formula VI:

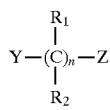

where Y, n, $R_1$ and $R_2$ have the same meaning as for the compound with the formula V and Z is a Cl or Br atom, to provide the compound with the formula VII.

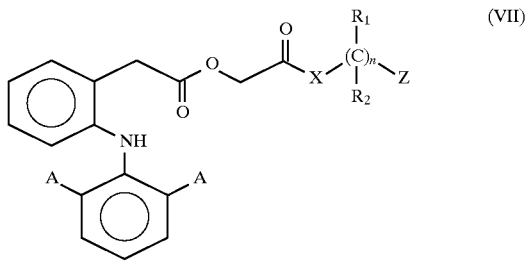

where A, X, $R_1$, $R_2$, n and Z have the meaning mentioned above.

The reaction is carried out, as mentioned in section i), by means of N,N'- dicyclohexylcarbodiimide or N,N'-carbonyl diimidazole as a condensation agent in the same conditions.

ii) Optional subsitution of the Z halogen of the compound with the formula VII for a iodine atom through the reaction with sodium iodine to provide the compound with the formula VIII.

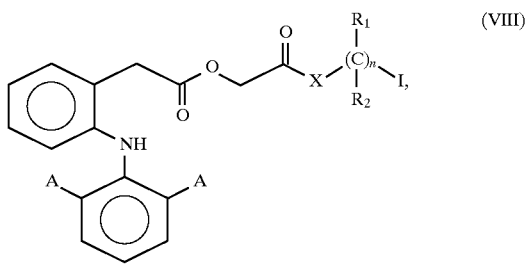

where A, X, $R_1$, $R_2$ and n have the same meaning as the one given to the compound with the general formula I.

iii) Displacement shift of the Z halogen with the formula VII or, otherwise, of the iodine atom I of the compound with the formula VIII with $AgNO_3$ in acetonitrile as solvent, to provide the corresponding nitroesters with the formula I.

The products with the formula I in this invention are obtained easily according to what has been said in the former description with a series of procedures with few stages which allow a preparation with a good performance and purely. All this is shown in the following examples:

EXAMPLE 1

Obtention of 2-nitrooxyethyl 2-(2,6-dichlorophenylamino) phenylacetoxyacetate

Solve 6.28 g (0,040 mol) of N,N'-carbonyl diimidazole in 150 ml of anhydrous dichloromethane under a dry nitrogen atmosphere. Shake and add for five minutes 13.87 g (0.039 mol) of the 2-(2,6-dichlorophenylamino) phenylacetoxyacetic acid in four shares.

Shake for five minutes and add a solution of 4.19 g (0.039 mol) of 2-nitrooxyethanol to 50 ml of dichloromethane. Protect from the light and shake for 18 hours. Eliminate the solvent under reduced pressure and solve again in 150 ml of ethyl acetate.

Wash three times with 100 ml of HCl 0.5N, twice with 100 ml of $NaHCO_3$ at 10% and neutralize washing twice with a saturated solution of NaCl. Dry on anhydrous sodium sulphate. Filter, eliminate the solvent at a reduced pressure and purify the oil obtained by chromatography in silica gel column.

Elute with dichloromethane and recover 11.92 g (69%) of 2-nitrooxyethyl 2-(2,6-dichlorophenylamino) phenylacetoxyacetate in form of oil that crystallizes (m.p. 61°–64° C.) and that has the following spectroscopic features:

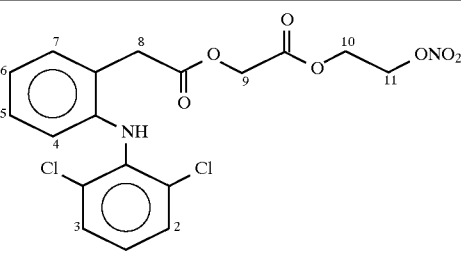

| | |
|---|---|
| IR (KBr, $cm^{-1}$): | 3360(N—H), 1744(C=O), 1640($ONO_2$) |
| $^1$H-RMN ($DCCl_3$, δ): | 3.95(S, 2H, $CH_2$(8)), 4.41(m, 2H, $CH_2$(11)), 4.59(m, 2H, $CH_2$(10)), 4.72(s, 2H, $CH_2$(9)), 6.57(d, 1H, $J_{4,5}$=7.8Hz, C—H(4)), 6.69(S, 1H, N—H), 6.98(m, 1H, $J_{6,7}$=$J_{6,5}$=7.8Hz, $J_{6,4}$=0.9Hz, C—H(6)), 6.99(t, 1H, $J_{1,2-3}$=8.1Hz, CH(1)), 7.15(m, 1H, $J_{5,4}$=$J_{5,6}$=7.8 Hz, $J_{5,7}$=1.8Hz, C—H(5)), 7.27(m, 1H, $J_{7,6}$=7.8Hz, $J_{7,5}$=1.8Hz, C—H(7), 7.35(d, 2H, $J_{2-3,1}$=8.1Hz, C—H(2)(3)). |
| $^{13}$C-RMN ($DCCl_3$, δ): | 37.94, 60.93, 61.01, 69.82, 118.42, 122.18, 123.71, 124.13, 128.21, 128.86, 129.49, 130,96, 137.73, 142.67, 167.13, 171.38. |
| EM (El, m/e): | 442(M)$^+$, 444(M + 2)$^+$, 446(M + 4)$^+$ |

EXAMPLE 2

Obtention of 3-nitrooxyethyl 2-(2,6-dichlorophenylamino) phenylacetoxyacetate

Solve 4.02 g (0,024 mol) of N,N'-carbonyl diimidazole in 30 ml of anhydrous chloroform under a dry nitrogen atmosphere.

Shake and add 8.78 g (0.024 mol) of 2-(2,6-dichlorophenylamino) phenylacetoxyacetic acid in three shares. Shake for five minutes and add a solution of 3 g (0.024 mol) of 3-nitrooxypropanol to 15 ml of chloroform. Protect from the light and shake for 16 hours under these conditions. Eliminate the solvent by means of rotating steam and solve again in 100 ml of ethyl acetate. Wash three times with 50 ml of HCl 1N, twice with a solution of $NaHCO_3$ at 10% and neutralize washing twice with water saturated with NaCl.

Dry on anhydrous sodium sulphate. Filter, eliminate the solvent at a reduced pressure to obtain an oil that crystallizes in methanol. Recover 5.99 g (54%) of 3-nitrooxypropyl 2-(2,6-dichlorophenylamino) phenylacetoxyacetate (m.p. 57°–59° C.) with the following spectroscopic features:

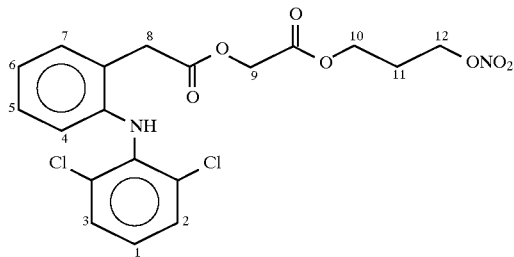

| | |
|---|---|
| IR (KBr, cm$^{-1}$): | 3360(N—H), 1755(O—CH$_2$—CO—O), 1743 (ArCH$_2$—CO—O), 1629(ONO$_2$). |
| $^1$H-RMN (DCCl$_3$, δ): | 1.97(m, 2H, J=6.3Hz, CH$_2$(11)), 3.93 (s, 2H, (8)), 4.22(t, 2H, J$_{10,11}$=6.1 Hz, CH$_2$(10)), 4.41(t, 2H, J$_{12,11}$=6.1 Hz, CH$_2$(12)), 4.69(s, 2H, CH$_2$(9)), 6.56(d, 1H, J$_{4,5}$=8.1Hz, C—H(4)), 6.72(s, 1H, N—H), 6.97(m, 1H, J$_{6,5}$=J$_{6,7}$=7.8Hz, J$_{6,4}$0.9Hz, C—H(6)), 6.99(t, 1H, J$_{1,2-3}$=8.1Hz C—H(1)), 7.14(m, 1H, J$_{5,6}$=J$_{5,4}$=7.8Hz, J$_{5,7}$=1.8Hz, C—H(5)), 7.27(m, 1H, J$_{7,6}$=7.8Hz, J$_{7,5}$=1.8Hz C—H(7)), 7.34(d, 2H, J$_{2-3,1}$=8.4Hz C—H(2)(3)). |
| $^{13}$C-RMN (DCCl$_3$, δ): | 26.12, 37.99, 61.15, 61.32, 69.37, 118.35, 122.13, 123.66, 124.16, 128.19, 128.86, 129.48, 130.93, 137.67, 142.67, 167.23, 171.42. |
| EM (El, m/e): | 456(M)$^+$, 458(M + 2)$^+$, 460(M + 4)$^+$. |

EXAMPLE 3

Obtention of 4-chlorobutyl 2-(2,6-dichlorophenylamino) phenylacetoxy-acetate Solve 6.48 g (0,040 mol) of N,N'-carbonyl diimidazole in 100 ml of anhydrous dichloromethane under a dry nitrogen atmosphere. Shake and add 13.86 g (0.039 mol) of 2-(2,6-dichlorophenylamino)phenylacetoxyacetic acid for five minutes in three shares.

Shake for five minutes and add a solution of 4.25 g (0.039 mol) of 4-chloro-1-butanol to 50 ml of dichloromethane. Protect from the light and shake for 20 hours.

Eliminate the solvent under reduced pressure and solve again the residue in 300 ml of ethyl acetate. Wash three times with 100 ml of HCl 1N, twice with a solution of NaHCO$_3$ at 10% and neutralize washing twice with a saturated solution of NaCl. Dry on anhydrous sodium sulphate.

Filter, eliminate the solvent at a reduced pressure and purify the oil obtained by chromatography in silica gel column. When eluting with dichloromethane recover 11.95 g (69%) of 4-chlorobutyl 2-(2,6-dichlorophenylamino) phenylacetoxyacetate in form of oil that has the following spectroscopic features:

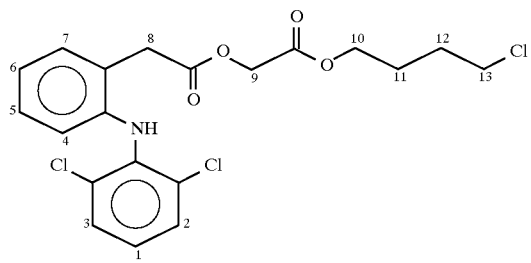

| | |
|---|---|
| IR(KBr, cm$^{-1}$): | 3360(N–H), 1742(C=0). |
| $^1$H-RMN(DCCl$_3$, δ): | 1.75(m, 4H, CH$_2$(11)), CH$_2$(12)), 3.50(t 2H, J$_{10,11}$=6HzCH$_2$(10)), 3.94(s, 2H, CH$_2$(8)), 4.17(t, 2H, J$_{13,12}$(13)), 4.68(s, 2H, CH$_2$(9)), 6.56(dd, 1H, J$_{4,5}$=7.8Hz, J$_{4,6}$-0.9Hz, C—H(4)), 6.74(s, 1H, N—H), 6.98 (m, 1H, J$_{6,5}$=J$_{6,4}$=1.2Hz, C—H (6)), 6.99(t, 1H, J$_{1,2-3}$=7.9Hz, C—H(1)), 7.14(m, 1H, J$_{5,6}$=J$_{5,4}$=7.4Hz, J$_{5,7}$=1.5Hz, C—H(5)), 7.27(dd, 1H, J$_{7,6}$=7.5Hz, J$_{7,5}$=1.2Hz, C—H(7)), 7.34(d, 2H, J$_{2-3,1}$=8.1Hz, C—H(2), C—H(3)). |
| $^{13}$C-RMN(DCCl$_3$, δ): | 25.64, 28.64, 37.92, 44.17, 61.11, 64.49, 118.30, 122.02, 123.97, 128.73, 129.38, 130.82, 1.37.64, 142.59, 167.30, 171.31. |
| EM(E1, m/3): | 443(M)$^+$, 445(M+2)$^+$, 447(M+4)$^+$. |

EXAMPLE 4

Obtention of 4-iodinebutyl 2-(2,6-dichlorophenylamino) phenylacetoxyacetate

Solve 8.84 g (0.019 mol) of 4-chlorobutyl 2-(2,6-dichlorophenylamino) phenylacetoxyacetate in 100 ml of anhydrous acetone, add 5.85 g (0.038 mol) of sodium iodide and warm by reflux for 40 hours. Cool it, filter the sodium chloride formed and eliminate the solvent at a reduced pressure. Solve again the residuem with a mixture of 150 ml of dichloromethane and 50 ml of water. Decant the organic phase and dry on anhydrous sodium sulphate.

Filter and concentrate by means of vacuum to have 10.76 g of an oil. When chromatographing it in a silica gel column, eluting with dichloromethane you recover 8.76 g (82%) of 4-iodinebutyl 2-(2,6-dichlorophenylamino) phenylacetoxyacetate in the form of an oil that has the following spectroscopic features:

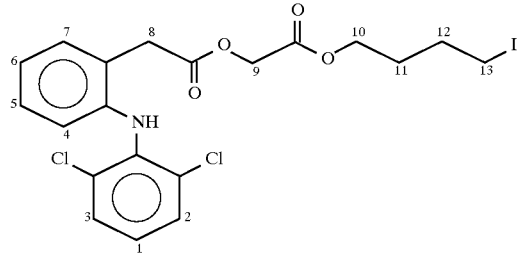

| | |
|---|---|
| IR(KBr, cm$^{-1}$): | 3360(N—H), 1746(C=O). |
| $^1$H-RMN(DCCl$_3$, δ): | 1.70(m, 2H, CH$_2$, (11)), 1.80(m, 2H, CH$_2$ (12)), 3.13(tJ$_{10,11}$=6.6Hz, 2H, CH$_2$(10)), 3.93(s, 2H, CH$_2$(8)), 4.15(t, J$_{13,12}$=6.6Hz, 2H, CH$_2$(13)), 4.67(s,2H,CH$_2$(9)), 6.56(dd, 1H, J$_{4,5}$=8.1Hz, J$_{4,6}$=1.2Hz, C—H(4)), 6.73 (s, 1H, N—H), 6.98(m, 1H, J$_{6,5}$=J$_{6,7}$=7.3Hz, J$_{6,4}$=1.2Hz, C—H(6)), 6.99(t, 1H, J$_{1,2-3}$=8.1Hz, C—H(1)), 7.14(m, 1H, J$_{5,6}$=J$_{5,4}$=7.8 Hz,J$_{5,7}$=1.5Hz, C—H(5)), 7.26(dd, 1H, J$_{7,6}$=7.6Hz, J$_{7,5}$1.5Hz, C—H(7)), 7.34(d, 2H, J$_{2-3,1}$=7.8Hz, C—H(2)(3)). |
| $^{-}$C-RMN(DCCl$_3$, δ): | 5.74, 29.26, 29.62, 38.06, 61.25, 64.25, 188.44, 122.17, 123.83, 124.11, 128.18, 128.87, 129.51, 130.96, 137.79, 142.72, 167.42, 171.43. |
| EM(E1, m/e): | 535(M)$^+$, 537(M+2)$^+$, 539(M+4)$^+$. |

EXAMPLE 5

Obtention of 4-nitrooxybutyl 2-(2,6-dichlorophenylamine) phenylacetoxyacetate.

A. Add for twenty minutes a solution of 8.35 g (0.015 mol) of 4-iodinebutyl 2-(2,6-dichlorophenylamine) phenylacetoxyacetate in 30 ml of acetonitrile to a solution of 3.26 g (0,019 mol) of silver nitrate in 50 ml of anhydrous acetonitrile, and shake for 18 hours.

Finally, warm by reflux for 3 more hours. Filter and wash the precipitate with 30 ml of acetonitrile and concentrate the filtrates at a reduced pressure.

Shake the residue with 80 ml of ethyl ether and filter. Eliminate the ether and purify the oil obtained by silica gel chromatography. When eluting with dichloromethane you recover 6.48 g (88%) of 4-nitrooxybutyl 2-(2,6-dichlorophenylamino) phenylacetoxyacetate in form of oil that has the following spectroscopic features:

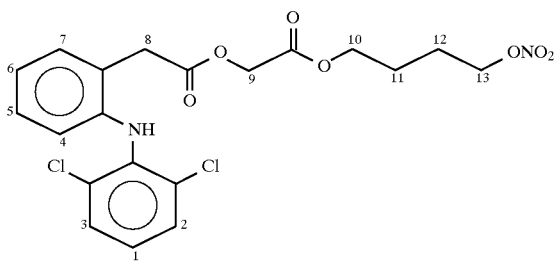

| | |
|---|---|
| IR(KBr, cm$^{-1}$): | 3360(N—H), 1743(C=O), 1630(ONO$_2$). |
| $^1$H—NMN(DDCl$_3$, δ): | 1.69(m, 4H, CH$_2$(11)(12)), 3.93(s, 2H, CH$_2$(8)), 4.16(t, 2H, J$_{10,11}$=6Hz, CH$_2$(10)), 4.39 (t, 2H, J$_{13,12}$=6Hz, CH$_2$(13)), 4.67(s, 2H, CH$_2$(9)), 5.55(d, 1H, J$_{4,5}$=7.8Hz, C—H(4)), 6.73(s, 1H, N—H), 6.97(m, 1H, J$_{6,7}$=J$_{6,5}$= 7.5Hz, J$_{6,4}$=0.9Hz, C—H(6)), 6.99(t, 1H, J$_{1,2-3}$=7.9Hz, C—H(1)), 7.14(m, 1H, J$_{5,6}$= J$_{5,4}$=7.5Hz, J$_{5,7}$=1.5Hz, C—H(5)), 7.26(m, 1H, J$_{7,6}$=6.9Hz, J$_{7,5}$=1.5Hz, C—H(7)), 7.34 (D, 2H, J$_{2-3,1}$=8.1Hz, C—H(2)(3)). |
| $^{13}$C-RMN(DCCl$_3$, δ): | 23.35, 24.76, 38.01, 61.21, 64.42, 72.37, 118.39 122.12, 123.76, 124.13, 128.16, 128.86, 129.49, 130.94, 137.73, 142.71, 167.36, 171.43. |
| EM(E1, m/me) | 470(M)$^+$, 472(M+2)$^+$, 474(M+4)$^+$. |

B. Add for twenty minutes a solution of 2.45 g (0.005 mol) of 4-chlorobutyl 2-(2,6-dichlorophenylamine) phenylacetoxyacetate in 15 ml of acetonitrile to a solution of 1.5 g (0,008 mol) of silver nitrate in 20 ml of anhydrous acetonitrile, and warm by reflux for 12 hours. Add 1.5 g (0.008 mol) of silver nitrate and warm for 7 more hours. Filter the precipitate and wash it with 20 ml of acetonitrile and concentrate at a reduced pressure. Treat the residuum with 50 ml of ether and filter. Eliminate the ether by means of rotating steam to have an oil that purifies by chromatography in column on silica gel. When eluting with dichloromethane you recover 1.61 g (62%) of 4-nitrobutyl 2-(2, 6-dichlorophenylamino) phenylacetoxyacetate in form of oil with spectroscopic features similar to the ones of the product obtained by method A.

EXAMPLE 6

Obtention of N-(2-nitrooxyethyl)-2-(2,6-cidhlorophenylamino) phenylacetooxyacetamid Solve 6.86 g (0.042 mol) of N,N'-carbonyl diimidazole in 150 ml of anhydrous dichloromethane, under a dry nitrogen atmosphere. Shake and add 15 g (0.042 mol) of 2-(2,6-dichlorophenylamino) phenylacetoxyacetic acid in four shares for five minutes. Shake for five minutes and add 7.16 g (0.042 mol) of 2-nitratooxyethylamine nitrate. Protect from the light and shake for 18 hours.

Eliminate the solvent by means of rotating steam and solve again the residue in 200 ml of ethyl acetate. Wash three times with 80 ml of HCl 1N, twice with NaHCO$_3$ at 10% and neutralize by washing twice with 80 ml of NaCl saturated solution. Dry on anhydrous sodium sulphate. Filter and eliminate the solvent at a reduced pressure to have an oil that crystallizes with toluene. Recover 6.60 g (35%) of N-(2-nitrooxyethyl)-2-(2,6-dichlorophenylamino) phenylacetoxyacetamid in form of crystals (m.p. 87°–88° C.) with the following spectroscopic features:

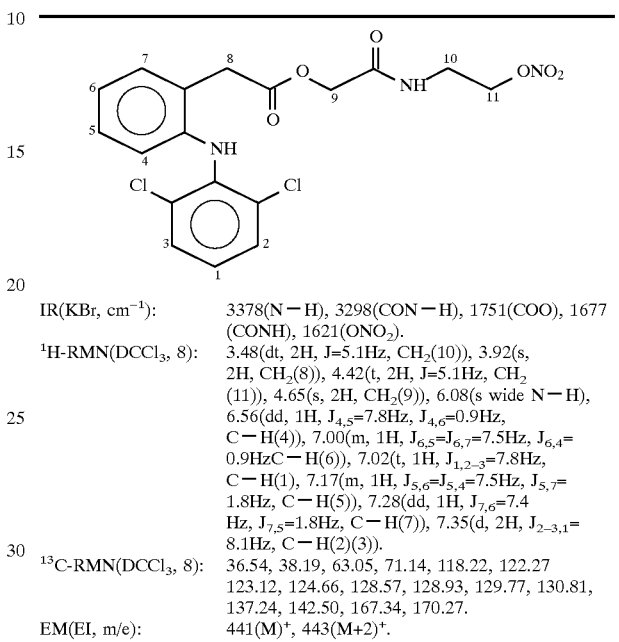

| | |
|---|---|
| IR(KBr, cm$^{-1}$): | 3378(N—H), 3298(CON—H), 1751(COO), 1677 (CONH), 1621(ONO$_2$). |
| $^1$H-RMN(DCCl$_3$, δ): | 3.48(dt, 2H, J=5.1Hz, CH$_2$(10)), 3.92(s, 2H, CH$_2$(8)), 4.42(t, 2H, J=5.1Hz, CH$_2$ (11)), 4.65(s, 2H, CH$_2$(9)), 6.08(s wide N—H), 6.56(dd, 1H, J$_{4,5}$=7.8Hz, J$_{4,6}$=0.9Hz, C—H(4)), 7.00(m, 1H, J$_{6,5}$=J$_{6,7}$=7.5Hz, J$_{6,4}$= 0.9HzC—H(6)), 7.02(t, 1H, J$_{1,2-3}$=7.8Hz, C—H(1), 7.17(m, 1H, J$_{5,6}$=J$_{5,4}$=7.5Hz, J$_{5,7}$= 1.8Hz, C—H(5)), 7.28(dd, 1H, J$_{7,6}$=7.4 Hz, J$_{7,5}$=1.8Hz, C—H(7)), 7.35(d, 2H, J$_{2-3,1}$= 8.1Hz, C—H(2)(3)). |
| $^{13}$C-RMN(DCCl$_3$, δ): | 36.54, 38.19, 63.05, 71.14, 118.22, 122.27 123.12, 124.66, 128.57, 128.93, 129.77, 130.81, 137.24, 142.50, 167.34, 170.27. |
| EM(EI, m/e): | 441(M)$^+$, 443(M+2)$^+$. |

We claim:

1. Nitric esters from derivatives of 2-(2,6-dihalophenylamino) phenylacetoxyacetic acid having the general formula (I):

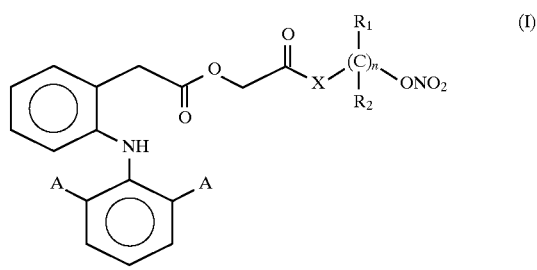

where:
A is fluorine, chlorine or bromine;
X is oxygen, NH or NR where R is a linear or branched alkyl chain of 1 to 6 carbon atoms;
R$_1$ and R$_2$ mean, independently, hydrogen or a linear or branched alkyl chain of 1 to 6 carbon atoms;
n is a number between 1 to 10.

2. Nitric esters from derivatives of 2-(2,6-dihalophenylamino) phenylacetoxyacetic acid according to claim 1, where A is chlorine, X is oxygen, R$_1$ and R$_2$ are both hydrogen and n is 2.

3. Nitric esters from derivatives of 2-(2,6-dihalophenylamino) phenylacetoxyacetic acid according to claim 1, where A is chlorine, X is oxygen, R$_1$ and R$_2$ are both hydrogen and n is 3.

4. Nitric esters from derivatives of 2-(2,6-dihalophenylamino) phenylacetoxyacetic acid according to claim 1, where A is chlorine, X is oxygen, $R_1$ and $R_2$ are both hydrogen and n is 4.

5. Nitric esters from derivatives of 2-(2,6-dihalophenylamino) phenylacetoxyacetic acid according to claim 1, where A is chlorine, X is NH, $R_1$ and $R_2$ are both hydrogen and n is 2.

6. Process of preparing nitric esters from derivatives of 2-(2,6-dihalophenylamino) phenylacetoxyacetic acid with the general formula (I):

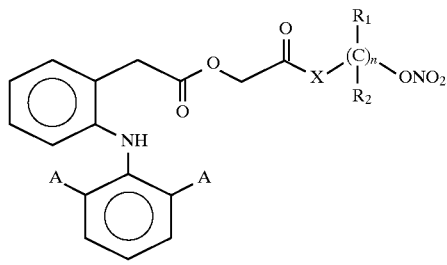

where:

A is fluorine, chlorine or bromine;

X is O, NH or NR where R is a linear or branched alkyl chain of 1 to 6 carbon atoms;

$R_1$ and $R_2$ mean, independently, hydrogen or a linear or branched alkyl chain of 1 to 6 carbon atoms;

n is a number between 1 to 10, characterized by condensing the 2-(2,6-dihalophenylamino) phenylacetoxyacetic acid with the formula (IV) where A is fluorine, chlorine or bromine

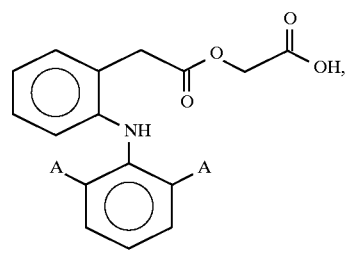

with a derivative with the general formula (V)

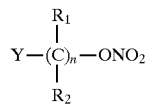

where Y can be OH, $NH_2$ or NHR, where R is a linear or branched alkyl chain of 1 to 6 carbon atoms, $R_1$ and $R_2$ mean, independently, hydrogen or a linear or branched alkyl chain of 1 to 6 carbon atoms and n is a number between 1 to 10, in presence of an suitable condenser agent in an aprotic organic solvent.

7. Process according to claim 6 which characterised in that the condenser agent is N,N'-carbonyl diimidazol.

8. Process of preparing nitric esters from derivatives of 2-(2,6-dihalophenylamino) phenylacetoxyacetic acid having the general formula (I):

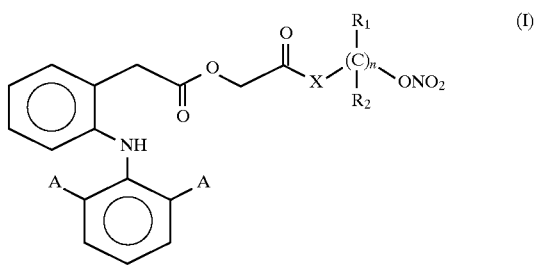

wherin:

A is fluorine, chlorine or bromine;

X means O, NH or NR where R means a linear or ramified alkyl chain of 1 to 6 carbon atoms;

$R_1$ and $R_2$ is, independently, hydrogen or a linear or branched alkyl chain of 1 to 6 carbon atoms;

n is a number between 1 to 10, characterized by having the following stages:
(i) condensation of 2-(2,6-dihalophenylamino) phenylacetoxyacetic acid with the formula IV:

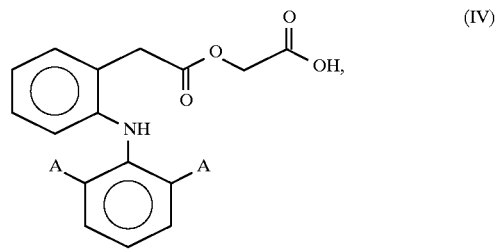

where:

A is fluorine, chlorine or bromine with a general formula compound with the formula VI:

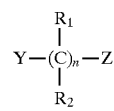

where Y is OH, $NH_2$ or NHR where R, $R_1$, $R_2$ and n have the meaning above mentioned and Z is chlorine or bromine, in presence of suitable condensation agent to provide the compound with the formula VII:

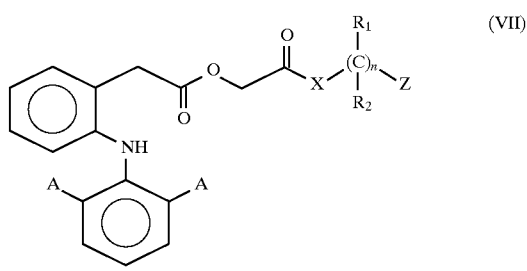

where A, $R_1$, $R_2$ and Z have the meaning above mentioned and X is O, NH or NR being R a linear or branched alkyl chain of 1 to 6 carbon atoms;
(ii) optional substitution of the Z halogen of the compound with the formula VII by a iodine atom through the reaction with sodium iodide to provide the compound with the formula VIII:

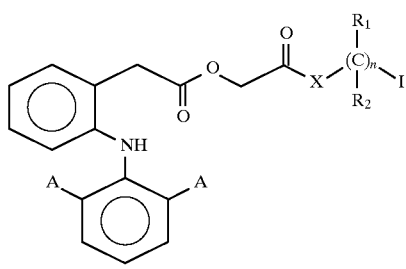
iii) displacement of the Z halogen of the compound with the formula VII or, otherwise, of the iodine atom I of the compound with the formula VIII with AgNO₃ in acetonitrile as solvent, to provide the corresponding nitroesters with the formula I.
9. Process according to claim 8 characterized in that the condensation agent in stage 1 is the N,N'-carbonyl diimidazole.
* * * * *